United States Patent [19]

Grams

[11] Patent Number: 4,552,813
[45] Date of Patent: Nov. 12, 1985

[54] METHOD OF INHIBITING THE GROWTH OF MARINE LIFE ON SURFACES IN CONTACT WITH SEAWATER

[76] Inventor: Ralph R. Grams, 2025 NW. 24th St., Gainesville, Fla. 32605

[21] Appl. No.: 534,499

[22] Filed: Sep. 21, 1983

Related U.S. Application Data

[63] Continuation of Ser. No. 348,504, Feb. 12, 1982, abandoned.

[51] Int. Cl.$^4$ ................................................ B32B 9/04
[52] U.S. Cl. ..................................... 428/411.1; 422/6; 427/385.5; 427/388.1; 427/389.8; 427/393; 428/907
[58] Field of Search ............... 427/385.5, 388.1, 388.4, 427/393, 389.8, 407.1; 428/15, 457, 537, 907, 411.1; 424/227; 106/18.32; 422/6

[56] References Cited

U.S. PATENT DOCUMENTS 2,997,471  8/1961  Cheney et al. ...................... 424/227
3,857,934  12/1974  Bernstein et al. ................... 428/907

FOREIGN PATENT DOCUMENTS 739439  7/1966  Canada ................................ 424/227

Primary Examiner—Sadie L. Childs
Attorney, Agent, or Firm—Arthur G. Yeager

[57] ABSTRACT

An antifouling coating for inhibiting the growth of marine life on surfaces in contact with seawater comprising a coating material having dispersed therein an effective amount of particles of a polycyclic naphthacenecarboxamide, preferably tetracycline. The principle use of composition of this invention is to coat the hulls of boats and ships and other surfaces contacted by seawater.

6 Claims, 1 Drawing Figure

METHOD OF INHIBITING THE GROWTH OF MARINE LIFE ON SURFACES IN CONTACT WITH SEAWATER

This application is a continuation of application Ser. No. 348,504, filed Feb. 12, 1982, abandoned.

BACKGROUND OF THE INVENTION

The hulls of ships, the surfaces of pilings, and other objects subjected to the activity of seawater inevitably become encrusted with various forms of marine life.

The marine life which cause the greatest problem are the crustaceous formations, such as barnacles, attaching themselves to the hulls of ships to cause a significant reduction in the speed with which the ship travels through the water. Among the many developments in this field are antifouling paints that inhibit the growth of such crustaceons, e.g. by incorporating mercury compounds in the paint to produce a toxic effect on the crustaceons. These materials however are pollutants that might cause undesirable effects on fish and other seafood which are eaten by humans. Furthermore, many of the available antifouling paints are effective for only a short period of time necessitating scraping and refinishing at frequent intervals in order to provide the desired protection.

In accordance with the present invention a new composition has been discovered which provides antifouling protection more effectively and for longer periods of time than has been known in the past. Since the expense of removing a ship from the water, scraping its hull, and repainting at frequent intervals is significant, it is an important improvement to provide a coating material which will minimize the downtime of the ship and that expenditure of money.

It is an object of this invention to provide an improved antifouling coating composition. It is another object of this invention to provide a method for preventing the growth of marine life on surfaces below sea water by applying to that surface a coating having an effective amount of a novel antifouling agent. It is another object of this invention to provide an antifouling agent which can be added to paint to produce an improved antifouling coating composition. Still other objects will be apparent from the more detailed description of this invention which follows.

BRIEF SUMMARY OF THE INVENTION

This invention provides a method for inhibiting the growth of marine life on surfaces in contact with seawater comprising covering that surface with a coating in which is embedded an effective amount of particles of a polycyclic naphthacenecarboxamide. Preferably, the coating is a paint and the embedded particles are tetracycline. This invention also provides an antifouling coating composition in which the coating material has dispersed therein an effective amount of particles of an antifouling agent as described above. In specific embodiments of this invention, the amount of antifouling agent is at least about 250 mg. of particles per quart of coating material and the particles are less than about 0.005 inch in diameter.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawing in which:

DETAILED DESCRIPTION OF THE INVENTION

Figure 1:
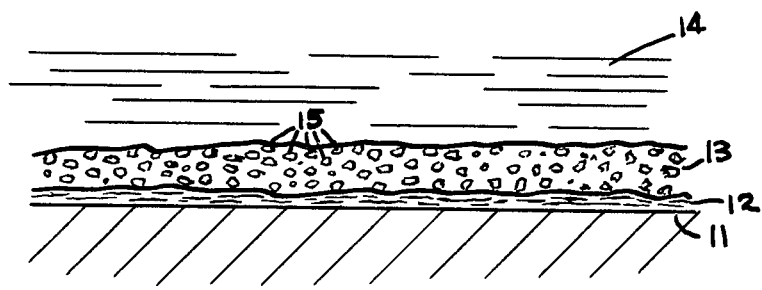
FIG. 1 is a schematic cross-sectional view of the coating in accord with this invention.

The antifouling agent of this invention is a polycyclic naphthacenecarboxamide in a particle size that is small enough to be readily dispersible in an oil-based paint. The family of polycyclic naphthacenecarboxamides includes tetracycline, chlorotetracycline, oxytetracycline, fluorotetracycline, bromotetracycline, demethylchlorotetracycline, demethyltetracycline, N-methyl-ethyl-oxytetracycline, 7-bromo-6-demethyltetracycline, 5-hydroxy-d-chlorotetracycline, N-methyl-ethyl-tetracycline, 6-a-deoxy-5-hydroxytetracycline, and their salts, hydrates, phosphates and the like. The preferred compound of this family of agents is tetracycline or any of its closely related derivatives such as salts, hydrates, phosphates, and the like.

The antifouling agent is used in the control of marine growth by being dispersed in a coating material which is then applied to a surface that is to be protected from marine growth. The most common application for this use is in an antifouling paint used on the hulls of boats to inhibit the growth of barnacles and other crustaceous formations. Other structures such as piling, docks, and the like, that are subjected to the action of seawater are usefully treated with the composition of this invention.

The base coating material to which the antifouling agent of this invention may be incorporated is preferably a high quality paint used on the hulls of ships or on any other structure that is subjected to the action of seawater. The coating, however, may be any other type of material such as a varnish, a plastic coating material, a molded plastic structure, etc. It is only necessary that the agent be intimately dispersed in the coating material so that the agent is available at the outer surface of the coating to inhibit the attachment of marine growth to the surface. In order to make the agent readily dispersible it is preferred that the agent be ground into a powder of small particle size, e.g. less than about 0.005 inch in diameter, and preferably about 0.001 to 0.004 inch in diameter. Whem the agent is ground to this small size it is readily dispersible in the paint or coating material and will be available at the surface to prevent the growth of marine life; and will continue to do so as the coating becomes worn or is abraded or flaked away to expose new particles of the antifouling agent that were previously completed embedded can then provide a continuing activity in preventing marine growth for a much longer period of time than other prior art antifouling paints.

It has been found that a very small amount of the antifouling agent is capable of performing the activity of preventing marine growth. As little as 250 mg. per quart of coating material is effective to prevent the growth of marine life. In order to provide an even better inhibitory effect it is preferred that the concentration of antifouling agent be between 250 mg. and 1.0 g. per quart of coating material with the most desirable concentration being about 500 mg. per quart. Higher concentrations than 1.0 g. per quart of coating material are effective in preventing marine growth, but are not preferred because of the additional expense and the increased solids content of the paint.

The coating composition of this invention may be prepared by any suitable methods and means which causes the dispersing of small particles of the antifouling agent throughout the basic coating material. In the preparation of an improved antifouling paint composition of this invention it is only necessary to obtain as a basic paint a good marine bottom paint, normally used to cover the hull of the ship, and to incorporate into the paint an effective amount of the antifouling agent of this invention. Any efficient type of stirring or shaking mechanism may be employed to disperse the antifouling agent throughout the paint composition. The paint is then ready to be applied in any known manner, such as brushing, rolling, spraying, or dipping, to the hull of the ship or to whatever structure that is to be covered thereby.

An illustrative depiction of the painted structure is shown in FIG. 1 wherein the structure itself, e.g. the surface of the hull of a ship is shown at 11 with whatever normal coating 12 that may be found on surface 11. If surface 11 is aluminum, layer 12 might be aluminum oxide. If surface 11 is wood, layer 12 might be a wood finish or a residue of impurities remaining after scraping the hull following a previous period of use in seawater. If surface 11 is fiberglass, layer 12 may be the remnants of a previous coating of paint. Coating 13 is the composition of this invention which protects surface 11 from the action of seawater 14. Coating 13 contains dispersed throughout its volume small particles 15 of the antifouling agent. Many of particles 15 are near the interface of coating 13 and seawater 14 and are continually leached by the seawater to provide an inhibitory action against the marine life in seawater 14 attaching itself to coating 13. It is believed that the long life and continuing effect of the antifouling composition of this invention is localized at the interface between coating 13 and seawater 14 as coating 13 is worn, eroded, or abraded, exposing new particles 15 to seawater 14. This leaching thereby provides the inhibitory effect at that interface.

In a series of actual tests to demonstrate the effectiveness of the antifouling agent and composition of this invention, a fiberglass cylinder approximately six feet long and one foot in diameter was sanded and finished with different compositions in four adjoining sections on the outside of the cylinder which was then suspended in seawater. One section of the cylinder was left uncoated, the second section of the cylinder was covered with a quality bottom paint for ships containing 250 mg. tetracycline per quart of paint. A third section of the cylinder was painted with the same type of bottom paint containing the same concentration of of sulfanilamide in place of tetracycline. A fourth section of the cylinder was painted with the same bottom paint except that penicillin was used in the same concentration rather than tetracycline. The cylinder was then suspended in seawater in an area near St. Augustine, Fla., where the marine growth problems are particularly acute, and observations were made during the succeeding year and a half. All during that time the second section which contained tetracycline in accordance with this invention remained absolutely clear and free of any marine growth. The two sections that were covered with paint containing sulfanilamide or penicillin exhibited some antifouling protection as evidenced by the fact that marine growth was present but was not heavily encrusted. The section of the cylinder which contained no coating was very heavily encrusted with barnacles and other marine life to a thickness of at least one inch.

In other experimental tests, the tetracycline or tetracycline hydrochloride was employed as an antifouling agent in ordinary house paint and applied to a cylinder and tested as described above. The marine growth was inhibited very well at concentrations of about 500 mg.–1.0 g. of agent per quart of paint, but the inhibitory effect was not quite as good as that found when the basic paint composition was a quality marine bottom paint.

It has been found that the inhibitory effect can be maintained over long periods of time if the surface of the antifouling composition of this invention is lightly brushed or sponged every two or three months to wipe off any minor accumulation of slime or the like which attaches itself by electrostatic forces to the submerged surface. It has been estimated that when treated in this manner the surface is free of marine growth at least 50% longer, and in many instances at least 100% longer, than that achieved by any prior known antifouling paints.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A method for inhibiting the growth of marine life on surfaces in contact with seawater comprising covering that surface with a suitable coating for seawater applications in which is dispersed an effective amount of particles of a polycyclic naphthacenecarboxamide available at the outer surface of the coating for contact by seawater.

2. The method of claim 1 wherein said coating is paint.

3. The method of claim 1 wherein said polycyclic napthacenecarboxamide is tetracycline.

4. The method of claim 1 wherein said effective amount is at least 250 mg. of particles per quart of coating.

5. The method of claim 1 wherein said particles are smaller than about 0.005 inch in diameter.

6. The method of claim 5 wherein said particles are from about 0.001 to about 0.004 inch in diameter.

* * * * *